(12) United States Patent
Ito et al.

(10) Patent No.: US 9,415,241 B2
(45) Date of Patent: Aug. 16, 2016

(54) CHARGED PARTICLE BEAM IRRADIATION SYSTEM

(71) Applicant: Hitachi, Ltd., Tokyo (JP)

(72) Inventors: Yuki Ito, Tokyo (JP); Koji Matsuda, Tokyo (JP); Ryosuke Shinagawa, Tokyo (JP); Masahiro Tadokoro, Tokyo (JP); Arao Nishimura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/625,662

(22) Filed: Feb. 19, 2015

(65) Prior Publication Data
US 2015/0273241 A1 Oct. 1, 2015

(30) Foreign Application Priority Data

Mar. 27, 2014 (JP) ................................ 2014-064969

(51) Int. Cl.
*G21K 5/04* (2006.01)
*A61N 5/10* (2006.01)

(52) U.S. Cl.
CPC .............. *A61N 5/1077* (2013.01); *A61N 5/103* (2013.01); *A61N 5/1043* (2013.01); *A61N 5/1067* (2013.01); *A61N 5/1071* (2013.01); *A61N 2005/1074* (2013.01); *A61N 2005/1087* (2013.01)

(58) Field of Classification Search
USPC ........ 250/396 R, 397, 396 ML, 492.1, 492.2, 250/492.21, 492.22, 492.23, 492.3
See application file for complete search history.

(56) References Cited

U.S. PATENT DOCUMENTS

2004/0227104 A1* 11/2004 Matsuda .................. A61N 5/10
  250/492.1
2014/0061498 A1 3/2014 Honda et al.

FOREIGN PATENT DOCUMENTS

JP 2005-050823 2/2005
JP 2011-177374 9/2011

OTHER PUBLICATIONS

Extended European Search Report received in corresponding European Application No. 151553231 dated Jun. 26, 2015.
Matsuda, K. et al., "World-First Proton Pencil Beam Scanning System with FDA Clearance-Completion of Proton Therapy System for MDACC-", Jan. 1, 2009, pp. 225-232, vol. 58, No. 5.

* cited by examiner

*Primary Examiner* — Nicole Ippolito
(74) *Attorney, Agent, or Firm* — Mattingly & Malur, PC

(57) ABSTRACT

The charged particle beam irradiation system includes a charged particle beam generating unit, scanning electromagnets, a beam irradiation apparatus, beam radiation dose measuring instrument(s), and a beam position measuring instrument for obtaining one or both of the position and the width of the beam scanned by the scanning electromagnets. The beam position measuring instrument obtains one or both of the position and the width of the beam for each irradiation spot and determines whether the obtained result is within an allowable range and obtains one or both of the position and the width of the charged particle beam for each split during irradiation to the spot with the charged particle beam regarding a split of which a dose is managed by dividing a part of or all of irradiation spots into irradiation sections and determines whether the obtained result is within an allowable range.

5 Claims, 7 Drawing Sheets

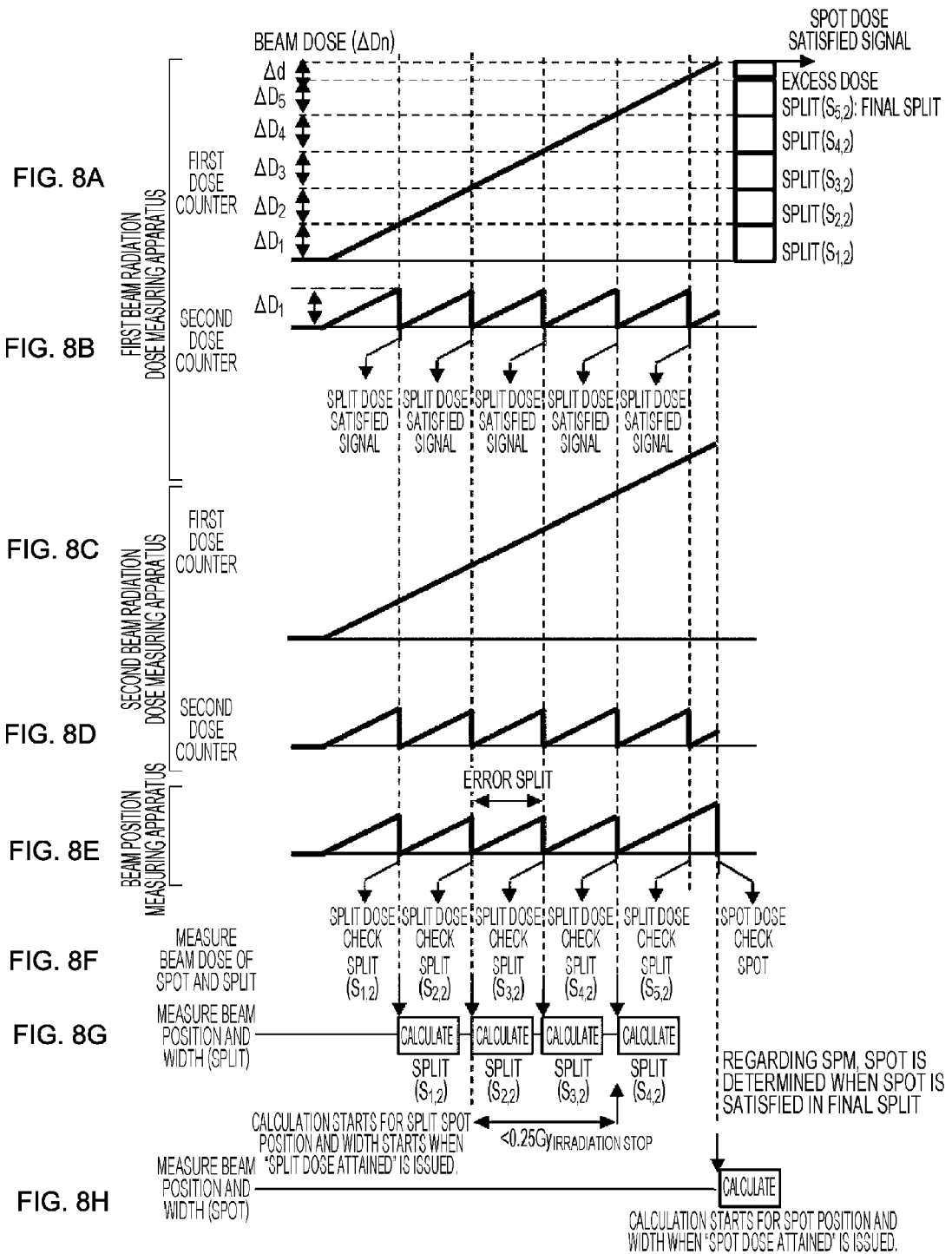

CHARGED PARTICLE BEAM IRRADIATION SYSTEM

BACKGROUND OF THE INVENTION

1. Field of the Invention

The present invention relates to a charged particle beam irradiation system for irradiating an affected part such as a tumor with a charged particle beam and treating the affected part.

2. Description of the Related Art

JP-2011-177374-A is considered as the related art of the present technique. JP-2011-177374-A discloses a charged particle beam irradiation system which can shorten an irradiation time in a particle beam treatment by a spot scanning method. The charged particle beam irradiation system includes a charged particle beam generating unit, beam transport unit(s), and beam irradiation apparatus(es). A controller calculates the position and the width of the charged particle beam from the output obtained by a beam position measuring apparatus in the beam irradiation apparatus every time when the irradiation to a spot has been completed.

SUMMARY OF THE INVENTION

In the treatment, it is desired to shorten treatment time in order to reduce a burden on a patient and increase the number of the patients to be treated. As one step of the spot scanning method, there is a method to shorten the irradiation time and improve the dose rate by increasing the irradiation dose which is applied to one irradiation section (spot) at one time and reducing the number of re-paints of the dose.

A characteristic of the present invention for solving the above-mentioned problem is a charged particle beam irradiation system including a charged particle beam generating unit configured to accelerate and extract a charged particle beam to an irradiation target, scanning electromagnets configured to scan the accelerated charged particle beam, beam irradiation apparatus(es) configured to irradiate the accelerated charged particle beam to a plurality of irradiation spots respectively set for a plurality of layers which is formed by dividing an irradiation target in a traveling direction of the charged particle beam, beam radiation dose measuring apparatus(s) configured to obtain a dose of the charged particle beam passing through the beam irradiation apparatus, and a beam position measuring instrument configured to obtain one or both of the position and the width of the charged particle beam scanned by the scanning electromagnets. The beam position measuring instrument obtains one or both of the position and the width of the charged particle beam for each irradiation spot, and the obtained results are judged whether they are within allowable ranges. In addition, the beam position measuring instrument obtains one or both of the position and the width of the charged particle beam for each split during irradiation to the irradiation spot with the charged particle beam with respect to a split of which a dose is managed by dividing a part of or all of the plurality of irradiation spots into a plurality of irradiation sections, and the obtained results are judged whether they are within allowable ranges.

According to the present invention, irradiation time of the charged particle beam relative to the irradiation target can be shortened.

BRIEF DESCRIPTION OF THE DRAWINGS

FIGS. 8(A) to 8(H) are diagrams, in which the irradiation spot No. 2 ($A_{i,2}$) in FIG. 4 is described as an example, of timings of the beam radiation dose measurement of the charged particle beam and the calculation of the position and the width of the beam performed by the charged particle beam irradiation system of a second embodiment in a spot and each split.

DESCRIPTION OF THE PREFERRED EMBODIMENTS

Embodiments will be described below with reference to the drawings.

First Embodiment

Figure 1:
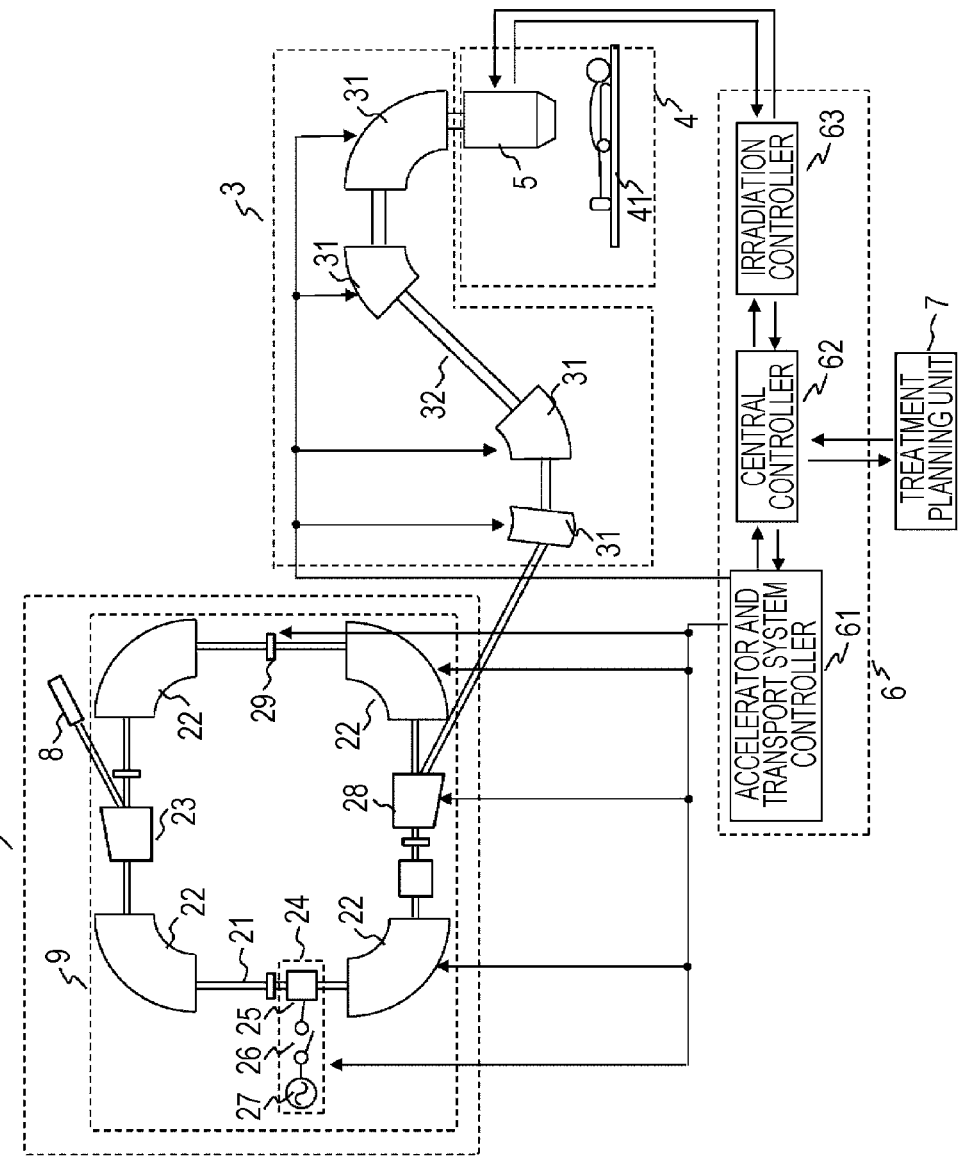
FIG. 1 is a schematic diagram of an overall construction of a charged particle beam irradiation system which is a preferred embodiment of the present invention.

A charged particle beam irradiation system which is one preferred embodiment of the present invention will be described with reference to FIG. 1. FIG. 1 is a schematic diagram of an overall construction of a charged particle beam irradiation system 1 according to the present embodiment. The charged particle beam irradiation system 1 uses a proton beam as a charged particle beam. An affected part of a cancer which is an irradiation target is irradiated with the charged particle beam. A heavy particle beam (for example, a carbon beam) may be used instead of the proton beam.

The charged particle beam irradiation system 1 includes a charged particle beam generating unit 2, beam transport unit(s) 3, beam irradiation apparatus(es) 5 and a controller 6. The beam irradiation apparatus 5 and a patient table 41 are arranged in a treatment room 4. The beam irradiation apparatus 5 is arranged opposed to the treatment table 41.

The charged particle beam generating unit 2 includes an ion source (not shown), a linear accelerator (linac) 8 which is a pre-accelerator, and a circular accelerator (synchrotron) 9. The linear accelerator 8 accelerates charged particles generated by the ion source until they become a predetermined energy and injects the pre-accelerated charged particles into the synchrotron 9. The synchrotron 9 accelerates the injected charged particles until they become a predetermined energy and the charged particles are extracted from the synchrotron 9. In the present embodiment, the synchrotron is exemplified as the circular accelerator. However, an accelerator, which does not have the pre-accelerator 8, such as a cyclotron or a synchro-cyclotron may be used instead of the synchrotron.

The synchrotron 9 includes a circular beam duct 21 for configuring an orbit of the charged particle beam, a plurality of bending electromagnets 22, a plurality of quadrupole electromagnets (not shown), an injector 23, a high frequency applying apparatus 24 for extraction, an extraction deflector 28, an acceleration unit (acceleration cavity) 29 which applies a high-frequency voltage to the charged particle beam. The high frequency applying apparatus 24 includes a pair of high-frequency electrodes 25 for extraction, an open/close switch 26, and a high-frequency power source 27. The high-frequency electrodes 25 is provided in the beam duct 21 and connected to the high-frequency power source 27 via the open/close switch 26. The acceleration unit 29, the plurality of bending electromagnets 22, the quadrupole electromagnets, and the extraction deflector 28 are arranged along the beam duct 21 as indicated in FIG. 1. A high-frequency power source apparatus (not shown) is connected to the acceleration unit 29.

The beam transport unit 3 includes a beam path (beam duct) 32 for connecting the synchrotron 9 with the beam irradiation apparatus 5. The beam transport unit 3 also includes a plurality of quadrupole electromagnets (not shown) and a plurality of bending electromagnets 31 on the beam path 32. The beam path 32 is connected to the circular beam duct 21 of the synchrotron 9 near the extraction deflector 28. The beam transport unit 3 delivers the charged particle beam accelerated by the charged particle beam generating unit 2 to the beam irradiation apparatus 5.

Figure 2:
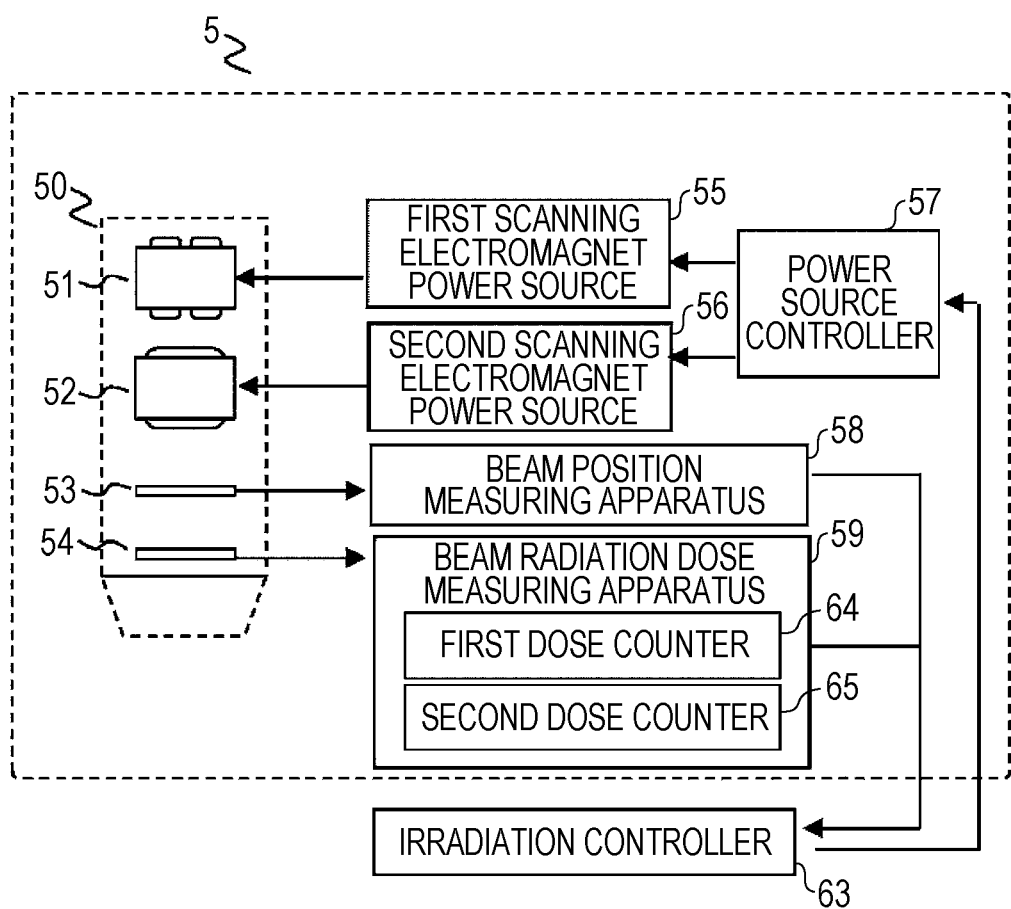
FIG. 2 is a schematic diagram of a construction of a beam irradiation apparatus and an irradiation controller included in the charged particle beam irradiation system of a first embodiment.

As indicated in FIG. 2, the beam irradiation apparatus 5 includes a casing 50, a first scanning electromagnet (X direction scanning electromagnet) 51, a second scanning electromagnet (Y direction scanning electromagnet) 52, a beam position detector (beam position monitor) 53, a beam radiation dose detector (beam dose monitor) 54, a first scanning electromagnet power source 55, a second scanning electromagnet power source 56, a power source controller 57, a beam position measuring apparatus 58, and a beam radiation dose measuring apparatus 59. The first and second scanning electromagnets 51 and 52, the beam position monitor 53, and the dose monitor 54 are arranged in the casing 50 and on a beam orbit of the charged particle beam passing through them.

One direction is referred to as an X direction and a direction perpendicular to the X direction is referred to as a Y direction on a surface perpendicular to the traveling direction of the charged particle beam delivered to the casing 50. The first scanning electromagnet 51 scans the charged particle beam passing through it in the X direction, and the second scanning electromagnet 52 scans the charged particle beam passing through it in the Y direction. The power source controller 57 controls the first scanning electromagnet power source 55 and the second scanning electromagnet power source 56 based on an instruction signal from the irradiation controller 63. The first scanning electromagnet power source 55 applies a predetermined exciting current to the first scanning electromagnet 51, and the second scanning electromagnet power source 56 applies a predetermined exciting current to the second scanning electromagnet 52.

The beam position monitor 53 and the beam dose monitor 54 are arranged in the casing 50 and a downstream (side of an exit of the casing 50) of the first scanning electromagnet 51 and the second scanning electromagnet 52. The beam position monitor 53 and the beam position measuring apparatus 58 are beam radiation dose measuring instruments for obtaining a position and a width of the charged particle beam. The beam position measuring apparatus 58 receives position data from the beam position monitor 53 and measures the position and the width (spread) of the passed charged particle beam. The beam dose monitor 54 and the beam radiation dose measuring apparatus 59 are beam radiation dose measuring instruments for measuring the beam radiation dose of the charged particle beam for passing through them. When receiving dose data from the dose monitor 54, the beam radiation dose measuring apparatus 59 measures the irradiation dose of the passed charged particle beam. The beam radiation dose measuring apparatus 59 has two dose counters (first dose counter 64 and second dose counter 65). The first dose counter 64 is reset immediately before or at the time of the start of the irradiation to an irradiation spot and constantly continues to count the irradiation dose of the charged particle beam during the irradiation to the same irradiation spot. When the irradiation dose reaches a target dose of the spot, the beam radiation dose measuring apparatus 59 outputs a spot dose satisfied signal to the central controller 62 and the irradiation controller 63. When the irradiation dose measured by the second dose counter 65 reaches a target dose OD which has been previously set, the beam radiation dose measuring apparatus 59 outputs a split dose satisfied signal to the central controller 62 and the irradiation controller 63, and at the same time, resets the count of the second dose counter 65. In the present embodiment, an example is described in which a beam position measuring instrument obtains both the position and the width of the charged particle beam. However, it may be an example in which the beam position measuring instrument obtains either one of the position or the width of the charged particle beam. Also, in the present embodiment, an example is described in which the beam irradiation apparatus 5 includes the beam position measuring apparatus 58 and the beam radiation dose measuring apparatus 59. However, the irradiation controller 63 may include the beam position measuring apparatus 58 and the beam radiation dose measuring apparatus 59.

The controller 6 includes an accelerator and transport system controller 61, a central controller 62, and an irradiation controller 63 as indicated in FIG. 1. The accelerator and transport system controller 61 and the irradiation controller 63 are connected to the central controller 62. The central controller 62 is connected to a treatment planning unit 7. The accelerator and transport system controller 61 controls each device included in the charged particle beam generating unit 2 and each device included in the beam transport unit 3. The irradiation controller 63 controls each device included in the beam irradiation apparatus 5.

Figure 3:
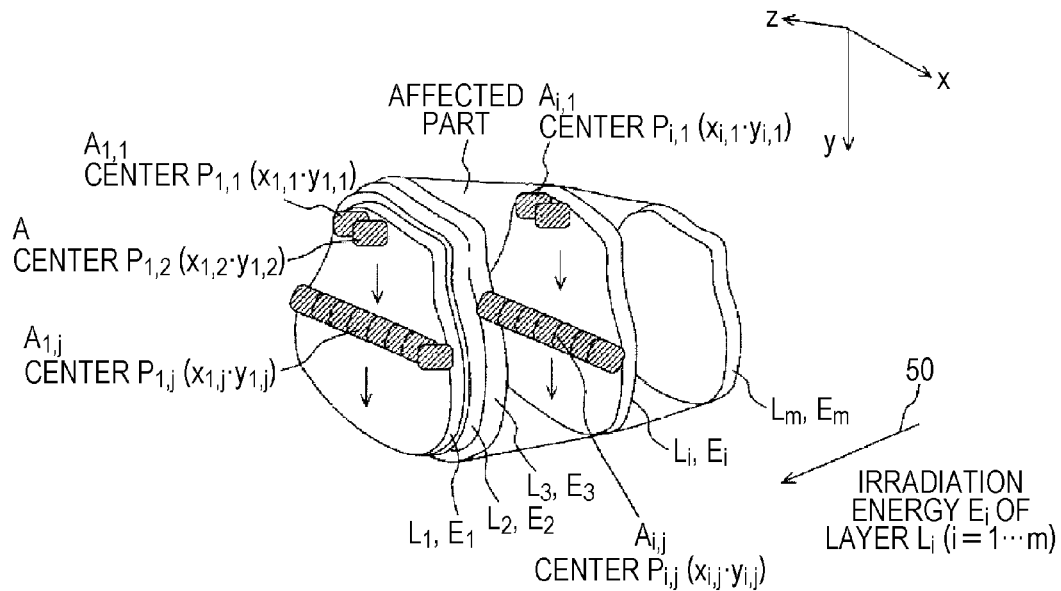
FIG. 3 is an explanatory diagram of division into regions (division into layers) in a depth direction from a body surface of an irradiation target which is irradiated with the charged particle beam.

The treatment planning unit 7 recognizes a position and shape of the irradiation target (for example, cancer affected part) by using tomographic image information obtained by photographing the patient by an X-ray CT scanner or the like. The treatment planning unit 7 determines a direction of the irradiation of the charged particle beam to the affected part and divides the irradiation target (affected part) into a plurality of layers $L_i$ (i=1, 2, . . . , m), that is, layers $L_1$, $L_2$, $L_3$, . . . , and $L_m$ in the direction of the irradiation (depth direction from a body surface of the patient) (FIG. 3). The layer $L_1$ exists at the deepest position from the body surface. The depth of the layer becomes shallower in an order of the layers $L_2$, $L_3$, . . . , and $L_m$, and the layer $L_m$ is the shallowest. The affected part is irradiated with the charged particle beam from a direction of an arrow 50. In addition, a plurality of irradiation spots $A_{i,j}$ (i=1, 2, . . . , m, j=1, 2, . . . , n) which is regions to be irradiated is set in each layer, and central positions (target position) $P_{i,j}$ and coordinates $(x_{i,j}, y_{i,j})$ of the central positions of these are set. Then, an order to irradiate the irradiation spots $A_{i,j}$ with the charged particle beam is determined. A target dose $R0_{i,j}$ for each irradiation spot $A_{i,j}$ is determined based on a necessary irradiation dose for the whole region to be irradiated. Energy $E_i$ of the charged particle beam is determined according to the depth of each layer so that the charged particle beam reaches each layer $L_i$ and the Bragg peak is formed for each layer. The treatment planning unit 7 prepares the treatment planning information before the treatment starts. The treatment planning information includes the number of layers $L_i$ of the irradiation target and irradiation spots $A_{i,j}$, the central position $P_{i,j}$ of the irradiation spot $A_{i,j}$, the target dose $R0_{i,j}$ for each irradiation spot $A_{i,j}$, the order of the irradiation to the irradiation spot $A_{i,j}$, the energy $E_i$ of the charged particle beam corresponding to each layer $L_i$, and the like.

The operation of the charged particle beam irradiation system 1 of the present embodiment will be described.

The central controller 62 receives the treatment planning information of the patient from the treatment planning unit 7 before the treatment starts. Also, the central controller 62 positions the treatment table 41 on which the patient stays at a predetermined position and arranges the table 41 so that the central axis of the beam irradiation apparatus 5 faces to the irradiation target of the patient on the treatment table 41.

When the positioning of the treatment table 41 has been completed, a medical worker (for example, a doctor) inputs a treatment start signal to an input device. When receiving the treatment start signal, the central controller 62 outputs a start command of preparation for the irradiation to the accelerator and transport system controller 61 and the irradiation controller 63. The accelerator and transport system controller 61 which has received the start command of preparation for the irradiation starts up the charged particle beam generating unit 2 and the beam transport unit 3 and starts the preparation for the irradiation of the charged particle beam. The accelerator and transport system controller 61 controls the charged particle beam generating unit 2 and the beam transport unit 3. Also, when receiving the start command of preparation for the irradiation, the irradiation controller 63 starts up the beam irradiation apparatus 5 and starts the preparation for the irradiation of the charged particle beam. The irradiation controller 63 controls the beam irradiation apparatus 5.

After the charged particles generated by the ion source have been accelerated by the linear accelerator 8, the accelerated charged particle is accelerated to a predetermined energy by the synchrotron 9. In the present embodiment, an irradiation method is described as an example in which the deepest layer $L_1$ of the irradiation target has been irradiated with the charged particle beam at first, and the layers $L_2$, $L_3$, . . . , $L_m$ are sequentially irradiated with the charged particle beam from the layer in the deep position to the layer in the shallow position after the respective target positions $P_{1,j}$ of all the irradiation spots $A_{1,j}$ in the layer $L_1$ has been irradiated with the charged particle beam. However, the irradiation method may be a method that the layers $L_m, L_{m-1}, \ldots, L_2$, and $L_1$ are sequentially irradiated with the charged particle beam from the layer in the shallow position to the layer in the deep position.

The irradiation controller 63 controls the exciting currents of the first scanning electromagnet 51 and the second scanning electromagnet 52 so that the charged particle beam is irradiated to the target position (central position) $P_{i,j}$ of the irradiation spot $A_{i,j}$. Specifically, the irradiation controller 63 outputs an exciting instruction signal to the power source controller 57 so that the exciting current is excited to the first scanning electromagnet 51 and the second scanning electromagnet 52. The exciting current is determined based on the information regarding the target position (central position) $P_{i,j}$ of the irradiation spot $A_{i,j}$. The power source controller 57 controls the first scanning electromagnet power source 55 and the second scanning electromagnet power source 56 to excite the exciting current to the first scanning electromagnet 51 and the second scanning electromagnet 52 respectively. The irradiation controller 63 controls the exciting currents of the first scanning electromagnet 51 and the second scanning electromagnet 52 so that the charged particle beam reaches a target position (central position) $P_{1,1}$ $(x_{1,1}, y_{1,1})$ of a first irradiation spot $A_{1,1}$ in the layer $L_1$.

When it is determined that the exciting currents of the first scanning electromagnet 51 and the second scanning electromagnet 52 have been adjusted so that the charged particle beam reaches the target position $P_{i,j}$ of the irradiation spot $A_{i,j}$, the irradiation controller 63 outputs a beam extraction start signal to the accelerator and transport system controller 61. When receiving the beam extraction start signal, the accelerator and transport system controller 61 extracts the accelerated charged particle beam from the synchrotron 9. The accelerated charged particle beam passes through the beam transport unit 3 and enters the beam irradiation apparatus 5.

The charged particle beam entered the beam irradiation apparatus 5 is scanned by the first scanning electromagnet 51 in the X direction and scanned by the second scanning electromagnet 52 in the Y direction so that the target position $P_{i,j}$ $(x_{i,j}, y_{i,j})$ of the irradiation spot $A_{i,j}$ in the layer $L_i$ of the irradiation target is irradiated with the charged particle beam.

The dose monitor 54 provided in the beam irradiation apparatus 5 measures the beam radiation dose of the charged particle beam, and the beam position monitor 53 measures the position and the width of the charged particle beam passing through it.

The dose monitor 54 outputs the measured dose data to the beam radiation dose measuring apparatus 59. The beam radiation dose measuring apparatus 59 inputs the received dose data to the first dose counter 64, obtains an cumulative dose $R_{i,j}$ to the irradiation spot $A_{i,j}$, and determines whether the cumulative dose $R_{i,j}$ reaches the target dose $R0_{i,j}$. When the cumulative dose $R_{i,j}$ does not reach the target dose $R0_{i,j}$ ($R_{i,j} > R0_{i,j}$), the irradiation spot $A_{i,j}$ is continuously irradiated with the charged particle beam. When the cumulative dose $R_{i,j}$ reaches the target dose $R0_{i,j}$, the beam radiation dose measuring apparatus 59 outputs the spot dose satisfied signal to the central controller 62 and the irradiation controller 63. The central controller 62 which has received the spot dose satisfied signal outputs a beam stop signal to the accelerator and transport system controller 61. The accelerator and transport system controller 61 stops the irradiation of the charged particle beam. When the irradiation spot $A_{i,j}$ is irradiated with the charged particle beam and the cumulative dose $R_{i,j}$ reaches the target dose $R0_{i,j}$, the extraction of the charged particle beam stops. Then, the exciting currents of the scanning electromagnets are changed in this state where the extraction of the charged particle beam stops. After the irradiation to the next irradiation spot with the charged particle beam has become possible, the extraction of the charged particle beam starts.

The beam position monitor 53 outputs the measured data of the position and the width to the beam position measuring apparatus 58. When the cumulative dose $R_{i,j}$ has reached the target dose $R0_{i,j}$, the beam position measuring apparatus 58 calculates the position and the width of the charged particle beam at the irradiation spot $A_{i,j}$ based on the received data of the position and the width and determines whether the position and the width are within a predetermined allowable range. When the position and the width of the charged particle beam is within the allowable range, the beam position measuring apparatus 58 determines that the irradiation to the irradiation spot $A_{i,j}$ has been normally completed and starts to irradiate the next irradiation spot $A_{i,j+1}$ with the charged particle beam. When the irradiation to all the irradiation spots in the layer $L_i$ with the charged particle beam has been completed, the next layer $L_{i+1}$ is irradiated with the charged particle beam. When all the layers $L_m$ of the irradiation target has been normally irradiated with the charged particle beam, the treatment for the patient ends. When the position and/or the width of the charged particle beam has exceeded the allowable range, the beam position measuring apparatus 58 determines that an abnormality occurs and outputs an abnormality detected signal to the accelerator and transport system controller 61, the irradiation controller 63, and the central controller 62. The accelerator and transport system controller 61 which has received the abnormality detected signal does not start to irradiate the next irradiation spot $A_{i,j+1}$ with the charged particle beam and terminates the beam irradiation.

The charged particle beam irradiation system 1 of the present embodiment determines the normality of the position and the width of the charged particle beam for each irradiation spot $A_{i,j}$ mentioned above. Additionally, the charged particle beam irradiation system 1 divides a part of or all of the irradiation spot $A_{i,j}$ from among the plurality of irradiation spots $A_{i,j}$ and determines the normality of the position and the width of the charged particle beam for each divided beam irradiation section $S_k$ (k=1, 2, . . . , p). This will be described in detail below with reference to FIGS. 4 to 6(F).

Figure 4:
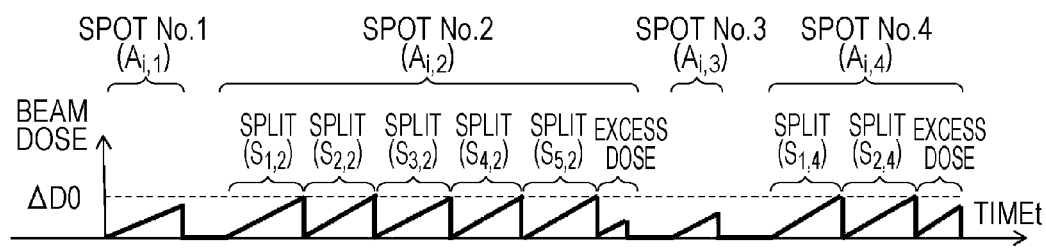
FIG. 4 is a diagram for describing an irradiation spot $A_{i,j}$ which is divided into a plurality of beam irradiation sections $S_k$ (split $S_k$) from among the irradiation spots $A_{i,j}$ in one layer $L_i$.

First, an irradiation spot $A_{i,j}$ which is divided into the plurality of beam irradiation sections $S_k$ (split $S_k$) from among the irradiation spots $A_{i,j}$ will be described. The description will be made with reference to FIG. 4 as an example. In FIG. 4, a spot No. 1 indicates a first irradiation spot $A_{i,1}$ of one layer $L_i$, and a spot No. 2 indicates a second irradiation spot $A_{i,2}$. A spot No. 3 indicates a third irradiation spot $A_{i,3}$, and a spot No. 4 indicates a fourth irradiation spot $A_{i,4}$. A horizontal axis in FIG. 4 indicates a time t. The charged particle beam irradiation system 1 sets the plurality of beam irradiation sections $S_k$ (split $S_k$) with respect to a part of or all the irradiation spots mentioned above (the second irradiation spot $A_{i,2}$ and the fourth irradiation spot $A_{i,4}$ in FIG. 4). For the purpose of the description, the beam irradiation section (split) which is set with respect to the j-th irradiation spot $A_{i,j}$ of one layer $L_i$ is indicated as $S_{k,j}$ (k=1, 2, . . . , p, j=1, 2, . . . , n).

The irradiation spot $A_{i,j}$ having the target dose $R0_{i,j}$ larger than the split target dose $\Delta D0$ is divided into the plurality of splits $S_{k,j}$. The irradiation spot $A_{i,j}$ having the target dose $R0_{i,j}$ smaller than the split target dose $\Delta D0$ is not divided into the plurality of splits. For example, it is assumed that the split target dose $\Delta D0$ be 0.033 MU. Since the irradiation spot No. 1 and the irradiation spot No. 3 have the target dose $R0_{i,j}$ smaller than the split target dose $\Delta D0$, they are not divided into the plurality of beam irradiation sections. Since the irradiation spot No. 2 and the irradiation spot No. 4 have the target dose larger than the split target dose D0, they are divided into the plurality of split $S_{k,j}$. The irradiation spot No. 2 is divided into the excess dose and five splits $S_{k,j}$, i.e., $(S_{1,2})$, $(S_{2,2})$, $(S_{3,2})$, $(S_{4,2})$, and $(S_{5,2})$. The irradiation spot No. 4 is divided into the excess dose and two splits $S_{k,j}$, i.e., $(S_{1,4})$ and $(S_{2,4})$. The respective beam irradiation sections $(S_{1,2})$, $(S_{2,2})$, $(S_{3,2})$, $(S_{4,2})$, $(S_{5,2})$, $(S_{1,4})$, and $(S_{2,4})$ are set to 0.033 MU. In the irradiation spot where one split $S_{k,j}$ or the plurality of splits $S_{k,j}$ is set, a beam irradiation section in which a place other than the set split $S_{k,j}$ is irradiated with the beam of the dose which is less than 0.033 MU is called as the excess dose. As described above, in the present embodiment, the irradiation spot $A_{i,j}$ divided into the plurality of beam irradiation sections (split) is determined based on a predetermined beam radiation dose (split target dose $\Delta D0$). Specifically, in a case where the target dose $R0_{i,j}$ of the irradiation spot $A_{i,j}$ is divided by the split target dose $\Delta D0$ and the result is fewer than one, the irradiation spot $A_{i,j}$ is not divided into the plurality of beam irradiation sections. In a case where the target dose $R0_{i,j}$ of the irradiation spot $A_{i,j}$ is divided by the split target dose $\Delta D0$ and the result is one or more, the target dose $R0_{i,j}$ of the irradiation spot $A_{i,j}$ is divided for each predetermined beam radiation dose (split target dose $\Delta D0$) so that the dose of all the beam irradiation sections becomes equal to or fewer than the predetermined beam radiation dose (split target dose $\Delta D0$).

When the splits $S_{k,j}$ set relative to one irradiation spot $A_{i,j}$ are irradiated with the charged particle beam, the target position $P_{i,j}$ of the charged particle beam which is determined by the first scanning electromagnet 51 and the second scanning electromagnet 52 is not changed even when the beam irradiation section changes (for example, from the split $(S_{1,2})$ to the other split $(S_{2,2})$). The target position $P_{i,j}$ of the next irradiation section $(S_{2,2})$ remains to be the target position $P_{i,j}$ of the irradiation spot $A_{i,j}$. The splits $S_{k,j}$ set relative to one irradiation spot $A_{i,j}$ are irradiated continuously with the charged particle beam. In the present embodiment, an example is described in which the irradiation spot $A_{i,j}$ to be divided into the plurality of beam irradiation sections $S_{k,j}$ (split $S_{k,j}$) is determined based on a predetermined beam radiation dose value. However, the irradiation spot $A_{i,j}$ may be divided into the plurality of beam irradiation sections $S_{k,j}$ (split $S_{k,j}$) based on a predetermined time interval instead of the predetermined beam radiation dose value. Also, the irradiation spot $A_{i,j}$ may be divided into the beam irradiation section $S_{k,j}$ (split $S_{k,j}$) by equally dividing the target irradiation dose $R0_{i,j}$ to the irradiation spot $A_{i,j}$ by using an integral quotient obtained when the target irradiation dose $R0_{i,j}$ to the irradiation spot $A_{i,j}$ is divided by the predetermined beam radiation dose value $\Delta D0$.

Figure 5:
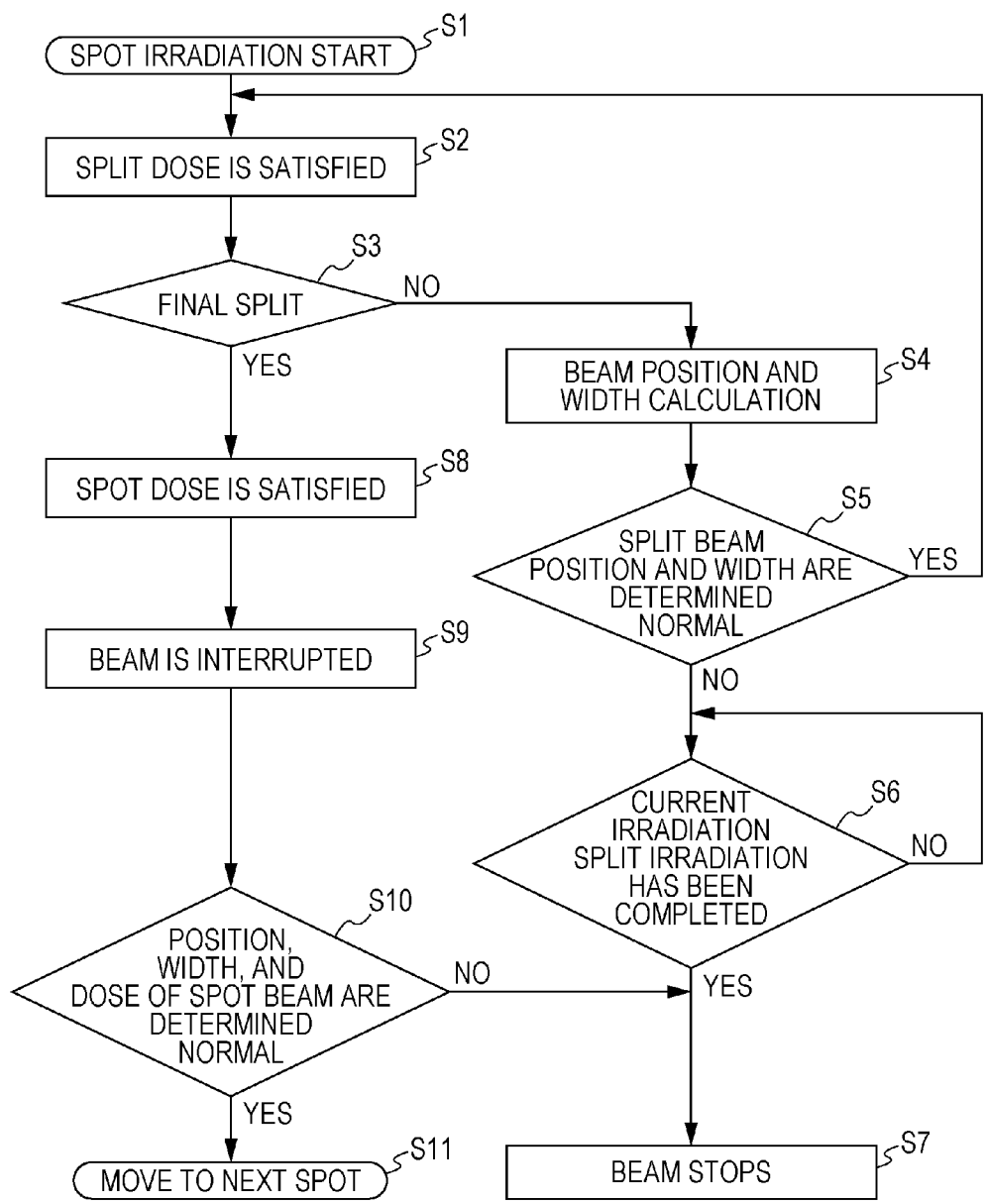
FIG. 5 is a flowchart of a flow for calculating the position and the width of the charged particle beam performed by the charged particle beam delivery system.
Figure 6:
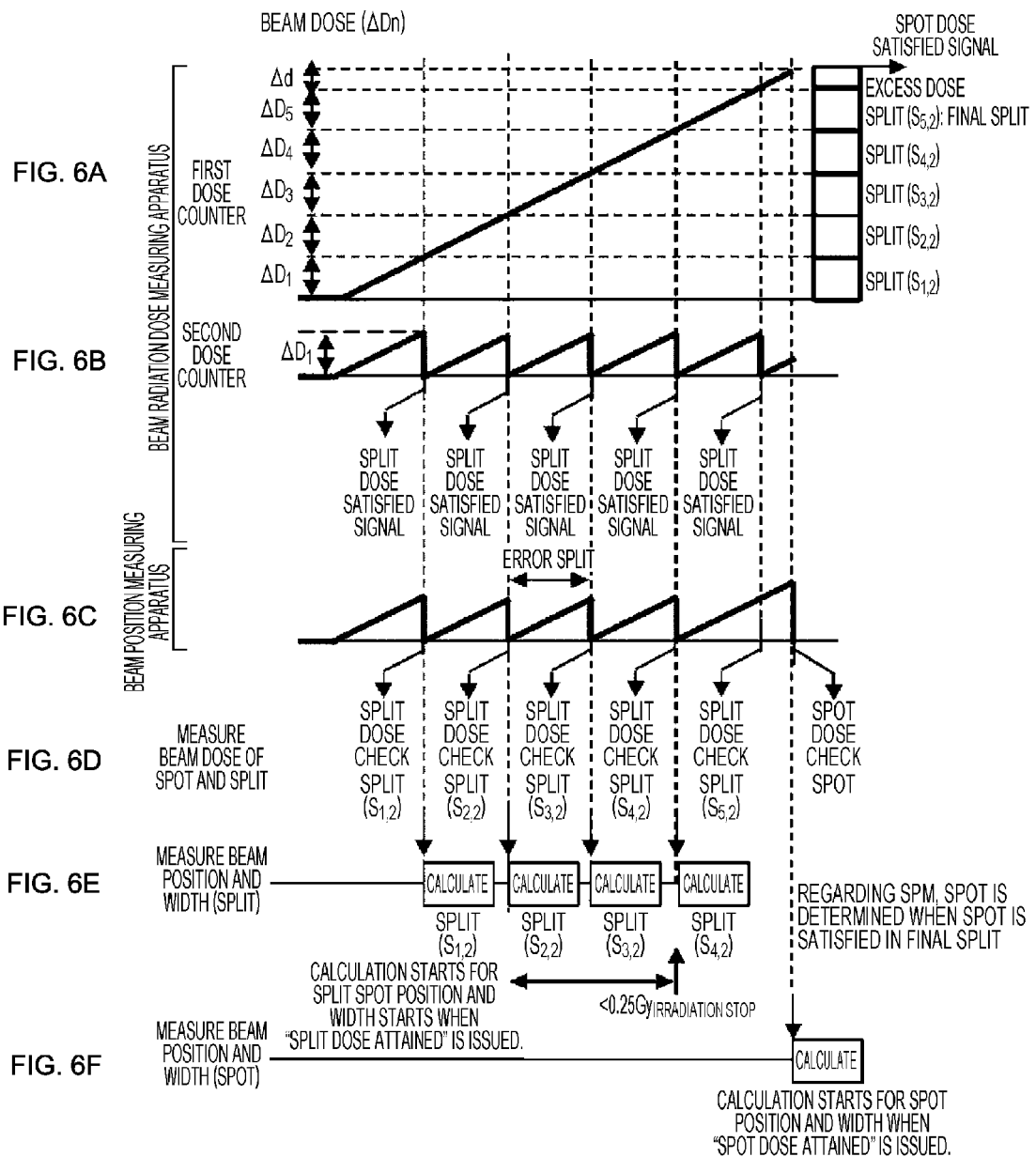
FIGS. 6(A) to 6(F) are diagrams, in which the irradiation spot No. 2 ($A_{i,2}$) in FIG. 4 is described as an example, of timings of beam radiation dose measurement of the charged particle beam and the calculation of the position and the width of the beam performed by the charged particle beam irradiation system of the first embodiment in a spot and each split.

It will be described with reference to FIGS. 5 to 6(F) that the charged particle beam irradiation system 1 according to the present embodiment calculates the position and the width of the charged particle beam in each beam irradiation section $S_{k,j}$ (split $S_{k,j}$). FIG. 5 is a flowchart for calculating the position and the width of the charged particle beam by the charged particle beam irradiation system 1 of the present embodiment. FIGS. 6(A) to 6(F) are diagrams of time-series timings of the beam radiation dose measurement of the charged particle beam and the calculation of the position and the width of the beam performed by the charged particle beam irradiation system 1 in the spot and each split. The irradiation spot No. 2 $(A_{i,2})$ illustrated in FIG. 4 is described as an example in FIGS. 6(A) to 6(F).

FIG. 6(A) indicates the measured result of the beam radiation dose by the first dose counter 64 of the beam radiation dose measuring apparatus 59, and FIG. 6(B) indicates the measured result of the beam radiation dose by the second dose counter 65 of the beam radiation dose measuring apparatus 59. As indicated in FIG. 6(A), when the beam cumulative dose $R_{i,j}$ to the irradiation spot reaches the target dose $R0_{i,j}$, the beam radiation dose measuring apparatus 59 outputs the spot dose satisfied signal to the central controller 62 and the irradiation controller 63. Also, as indicated in FIG. 6(B), when the beam radiation dose in each split reaches the target dose $\Delta D_k$, the beam radiation dose measuring apparatus 59 outputs the split dose satisfied signal to the irradiation controller 63. FIG. 6(C) is the measured result of the beam position in each split measured by the beam position measuring apparatus 58. FIG. 6(D) is a timing when the beam radiation dose measuring apparatus 59 measures the beam radiation dose in each split and the beam cumulative dose in the spot and determines their normality. FIG. 6(E) is a timing when the beam position measuring apparatus 58 calculates the position and the width of the beam in the split. FIG. 6(F) is a timing when the beam position measuring apparatus 58 calculates the position and the width of the beam in the spot and determines their normality.

The charged particle beam irradiation system 1 starts to irradiate the irradiation spot $A_{i,j}$ with the charged particle beam (step S1). The dose monitor 54 starts to measure the beam radiation dose of the charged particle beam, and the beam position monitor 53 starts to measure the position and the width of the passing charged particle beam. The dose monitor 54 outputs the measured dose data to the beam radiation dose measuring apparatus 59. The beam radiation dose measuring apparatus 59 inputs the received dose data to the second dose counter 65, and the second dose counter 65 obtains the beam radiation dose in each split. The beam radiation dose measuring apparatus 59 stores information on the target dose $\Delta D_k$ which has been previously set for each beam irradiation section $S_{k,j}$ (split $S_{k,j}$) in a memory (not shown). The beam radiation dose measuring apparatus 59 determines whether the beam radiation dose obtained by the second dose counter 65 has reached the target dose $\Delta D_k$ (step S2). When the beam radiation dose of the beam irradiation section $S_{k,j}$ (split $S_{k,j}$) reaches the target dose $\Delta D_k$, the beam radiation dose measuring apparatus 59 outputs the split dose satisfied signal to the irradiation controller 63 and resets the count of the second dose counter 65. In this way, when the beam radiation dose measuring apparatus 59 starts to obtain the beam irradiation dose of the next beam irradiation section, the beam radiation dose measuring apparatus 59 resets the second dose counter 65 and measures the beam radiation dose from zero in the next beam irradiation section. In this way, the second dose counter 65 measures the beam radiation dose for each beam irradiation section.

The irradiation controller 63 previously calculates the number of the split doses into which the target dose to the irradiation spot $A_{i,j}$ is divided and stores it in the memory (not shown). When receiving the split dose satisfied signal from the beam radiation dose measuring apparatus 59, the irradiation controller 63 determines whether the split dose satisfied signal is the split dose satisfied signal of the final split (step S3). When the split dose satisfied signal is not the split dose satisfied signal of the final split, the irradiation controller 63 does not interrupt the charged particle beam (continue the beam irradiation). When the split is not the final split, the beam radiation dose measuring apparatus 59 calculates the position and the width of the charged particle beam of the beam irradiation section $S_{k,j}$ which has been most recently irradiated (step S4). The beam radiation dose measuring apparatus 59 determines whether the position and the width of the beam according to the calculation result are within the allowable range (step S5). When this determination departs from the allowable range, the beam radiation dose measuring apparatus 59 outputs the abnormality detected signal to the accelerator and transport system controller 61, the central controller 62, and the irradiation controller 63. The irradiation controller 63 terminates to irradiate with the charged particle beam (step S7) immediately or at the same time when the next split dose satisfied signal is received (step S6).

When the split dose satisfied signal is the split dose satisfied signal of the final split, the beam position measuring apparatus 58 does not calculate the position and the width of the charged particle beam. Accordingly, the beam radiation dose $\Delta D_k$ of the final split and the dose $\Delta d$ which becomes excess when the target dose are divided by the split dose are not calculated and determined their positions and widths individually. The beam radiation dose of the final split is evaluated and determined as the cumulative dose of the whole spot after the spot irradiation has been completed. Therefore, a value of the split dose $\Delta D0$ is set so that the effect on the whole dose and dose distribution by the irradiation of the split dose $\Delta D0$ does not depart from the allowable range even when an abnormality occurs in the position and the width during the irradiation of the split dose $\Delta D0$.

Also, in a case where the next split dose satisfied signal has been output when the beam position measuring apparatus 58 has been calculating the position and the width of the charged particle beam and determining their normality in each split, it is preferable that the charged particle beam irradiation system 1 have an interlock for interrupting or terminating the irradiation with the charged particle beam. Alternatively, the control to limit the intensity of the charged particle beam may be performed so that the next split dose is not satisfied when the position and the width of the charged particle beam which is the integration of the split dose is calculated and determined.

In the present embodiment, as described above, the irradiating target dose for a single spot is divided into the plurality of split doses, and the beam position and the width of the charged particle beam is calculated for each split dose and determined (determination as to whether the calculation result of the beam position and the width departs from the allowable range). Then, even when an abnormality occurs in the beam position and the width of the charged particle beam during the irradiation to the single spot, it becomes possible to safely stop the beam irradiation before the influence of the abnormality departs from the allowable range. Accordingly, the limitation to the maximum dose with which the single spot can be irradiated can be considerably relaxed.

Also, according to the present embodiment, the upper limit of the dose with which a single irradiation spot can be irradiated is relaxed, while ensuring safety. The number of spot determinations is reduced in which the irradiation is interrupted by reducing the number of re-paints, and a dose rate is improved.

Second Embodiment

A charged particle beam irradiation system 1A of the present embodiment will be described. The charged particle beam irradiation system 1A of the present embodiment has a structure including a beam irradiation apparatus 5A instead of the beam irradiation apparatus 5 of the first embodiment. In the charged particle beam irradiation system 1A of the present embodiment, the description of parts, which have the same functions and are denoted with the same references as those in the configuration described in the first embodiment, is omitted.

Figure 7:
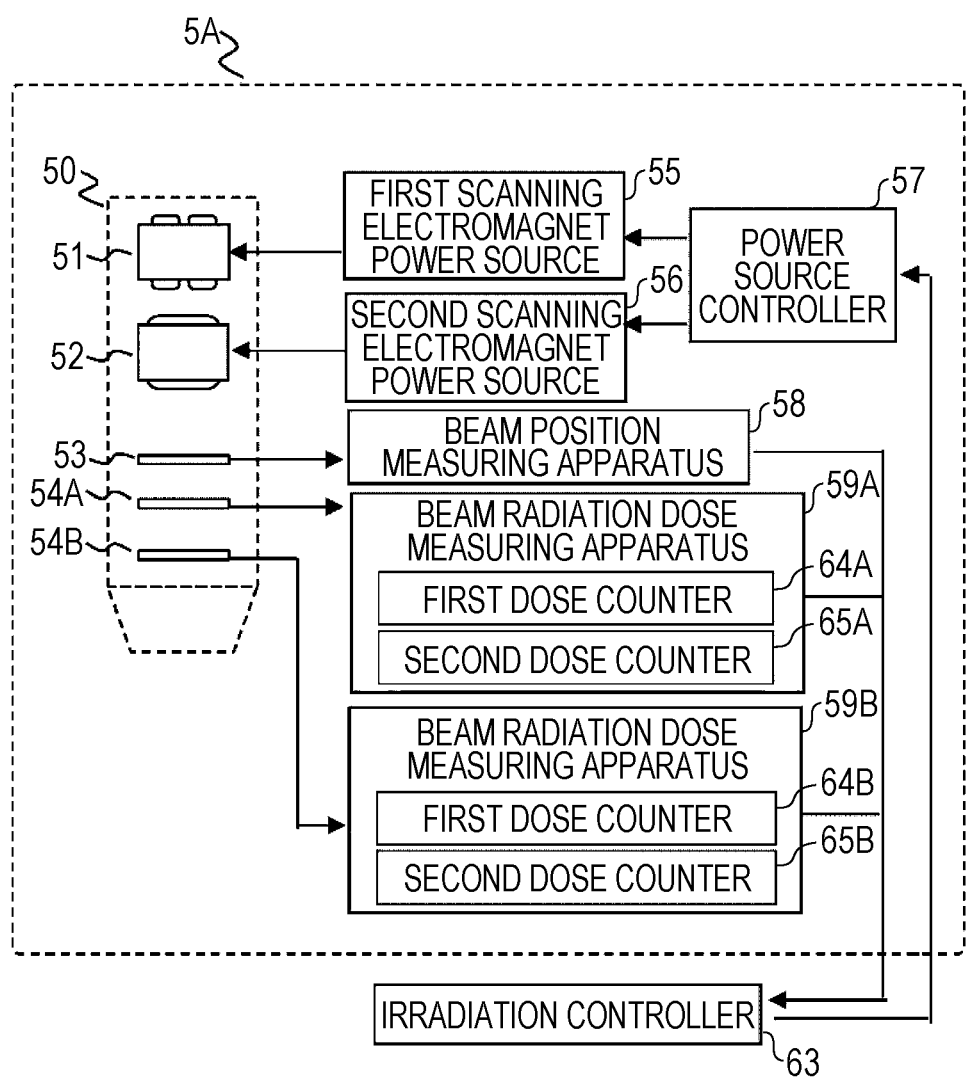
FIG. 7 a schematic diagram of a construction of a beam irradiation apparatus and an irradiation controller included in the charged particle beam irradiation system of a second embodiment.

The beam irradiation apparatus 5A of the present embodiment will be described with reference to FIG. 7. The beam irradiation apparatus 5A has a structure including two dose monitors (first dose monitor 54A and second dose monitor 54B) instead of the dose monitor 54 of the beam irradiation apparatus 5 of the first embodiment and including two beam radiation dose measuring apparatuses (first beam radiation dose measuring apparatus 59A and second beam radiation dose measuring apparatus 59B) instead of the beam radiation dose measuring apparatus 59 of the first embodiment. The first dose monitor 54A is connected to the first beam radiation dose measuring apparatus 59A, and the second dose monitor 54B is connected to the second beam radiation dose measuring apparatus 59B. The first beam radiation dose measuring apparatus 59A includes two dose counters (first dose counter 64A and second dose counter 65A). The second beam radiation dose measuring apparatus 59B includes two dose counters (first dose counter 64B and second dose counter 65B). The first dose monitor 54A and the first beam radiation dose measuring apparatus 59A are included in a first beam radiation dose measuring instrument, and the second dose monitor 54B and the second beam radiation dose measuring apparatus 59B are included in a second beam radiation dose measuring instrument. In the present embodiment, an example is described in which the first dose monitor 54A is arranged in the downstream of the second dose monitor 54B (a side of an exit of the beam irradiation apparatus 5A). However, the second dose monitor 54B may be arranged in the downstream of the first dose monitor 54A (the side of the exit of the beam irradiation apparatus 5A).

It will be described with reference to FIGS. 8(A) to 8(H) that the charged particle beam irradiation system 1A according to the present embodiment calculates the position and the width of the charged particle beam in each beam irradiation section $S_{k,j}$ (split $S_{k,j}$). FIGS. 8(A) to 8(H) are diagrams of time-series timings of the beam radiation dose measurement of the charged particle beam and the calculation of the position and the width of the beam performed by the charged particle beam irradiation system 1A in the spot and each split. In the present embodiment, an irradiation spot No. 2 ($A_{i,2}$) in FIG. 4 is described as an example with reference to FIGS. 8(A) to 8(H).

FIG. 8(A) indicates the measured result of the beam radiation dose by the first dose counter 64A of the first beam radiation dose measuring apparatus 59A, and FIG. 8(B) indicates the measured result of the beam radiation dose by the second dose counter 65A of the first beam radiation dose measuring apparatus 59A. As indicated in FIG. 8(A), when the beam cumulative dose $R_{i,j}$ to the irradiation spot reaches the target dose $R0_{i,j}$, the first beam radiation dose measuring apparatus 59A outputs the spot dose satisfied signal to the central controller 62 and the irradiation controller 63. Also, as indicated in FIG. 8(B), when the beam radiation dose in each split reaches the target dose $\Delta D_k$, the first beam radiation dose measuring apparatus 59A outputs the split dose satisfied signal to the irradiation controller 63.

FIG. 8(C) indicates the measured result of the beam radiation dose by the first dose counter 64B of the second beam radiation dose measuring apparatus 59B, and FIG. 8(D) indicates the measured result of the beam radiation dose by the second dose counter 65A of the beam radiation dose measuring apparatus 59B.

FIG. 8(E) indicates a storage of beam position information in each split by a position counter (not shown) of the beam position measuring apparatus 58.

FIG. 8(F) indicates a timing when the first beam radiation dose measuring apparatus 59A and the second beam radiation dose measuring apparatus 59B measure the beam radiation dose in each split and the beam cumulative dose in the spot. FIG. 8(G) indicates a timing when the beam position measuring apparatus 58 calculates the position and the width of the beam in the split, and FIG. 8(H) indicates a timing when the beam position measuring apparatus 58 calculates the position and the width of the beam in the spot.

In the present embodiment, two beam radiation dose measuring instruments, i.e., the first and second beam radiation dose measuring instruments, measure a dose value of the charged particle beam. A safer charged particle beam irradiation system can be provided by managing the beam radiation dose value by the two beam radiation dose measuring instruments.

According to the present embodiment, the irradiating target dose for a single spot is divided into the plurality of split doses, and the beam position and the width of the charged particle beam is calculated for each split dose and determined (determination as to whether the calculation result of the beam position and the width departs from the allowable range). Then, even when an abnormality occurs in the beam position and the width of the charged particle beam during the irradiation to the single spot, it becomes possible to safely stop the beam irradiation before the influence of the abnormality departs from the allowable range. Accordingly, the limitation to the maximum dose with which the single spot can be irradiated can be considerably relaxed.

According to the present embodiment, the upper limit of the dose with which a single irradiation spot can be irradiated is relaxed, while ensuring safety. The number of spot determinations is reduced in which the irradiation is interrupted by reducing the number of re-paints, and a dose rate is improved.

In the first and second embodiments, an example has been described in which the beam position measuring instruments (beam position monitor 53 and beam position measuring apparatus 58) obtain both the position and the width of the charged particle beam and determines the abnormality. However, one of the position and the width of the charged particle beam may be obtained and determined its abnormality.

What is claimed is:
1. A charged particle beam irradiation system comprising:
an ion source generating charged particles and an accelerator configured to accelerate and extract a charged particle beam;
a scanning electromagnet configured to scan the accelerated charged particle beam;
a controller, coupled to the scanning electromagnet, programmed to divide an irradiation target into a plurality of layers in a traveling direction of the charged particle beam and set a plurality of irradiation spots in the plurality of layers;
a beam irradiation apparatus, coupled to the controller, configured to irradiate the accelerated charged particle beam to the plurality of irradiation spots respectively set for the plurality of layers;
a beam radiation dose monitor, coupled to the controller, configured to obtain a dose of the charged particle beam passing through the beam irradiation apparatus; and
a beam position monitor, coupled to the controller, configured to obtain at least one of a position and a width of the charged particle beam scanned by the scanning electromagnet,
wherein the beam position monitor obtains at least one of the position and the width of the charged particle beam for each irradiation spot,
wherein the controller is programmed to:
determine whether the at least one of the position and the width of the charged particle beam obtained for each irradiation spot is within a first allowable range,
divide one or more of the plurality of irradiation spots into a plurality of splits and obtain at least one of the position and the width of the charged particle beam for each split,
determine whether the at least one of the position and the width of the charged particle beam of a split of an irradiation spot of the one or more of the plurality of irradiation spots is within a second allowable range, and after the determination of whether the least one of the position and the width of the charged particle beam of the split is within the second allowable range, determine whether the at least one of the position and the width of the charged particle beam of a subsequent split of the irradiation spot is within the second allowable range, and stop irradiation of the charged particle beam when the at least one of the position and the width of the charged particle beam for a split of the splits of an irradiation spot is not within the second allowable range, wherein the beam irradiation apparatus is configured to irradiate the plurality of irradiation spots in accordance with the results of the determinations for each of the first allowable range and the second allowable range.

2. The charged particle beam irradiation system according to claim 1, wherein
a split of the plurality of splits of an irradiation spot is set based on a predetermined reference dose value of the charged particle beam.

3. The charged particle beam irradiation system according to claim 1, wherein
the split is set based on predetermined time information.

4. The charged particle beam irradiation system according to claim 1, wherein
the split is set by equally dividing a target irradiation dose to the irradiation spot by using an integral quotient obtained when the target irradiation dose to an irradiation spot is divided by a reference dose value.

5. The charged particle beam irradiation system according to claim 1, wherein
the controller is further programmed to:
determine whether a split of a plurality of splits of a spot is a final split, determine whether the at least one of the position and the width of the beam of the final split is within the second allowable range based on information regarding at least one of the position and the width of the charged particle beam obtained in the irradiation spot.

\* \* \* \* \*